Figure 1:
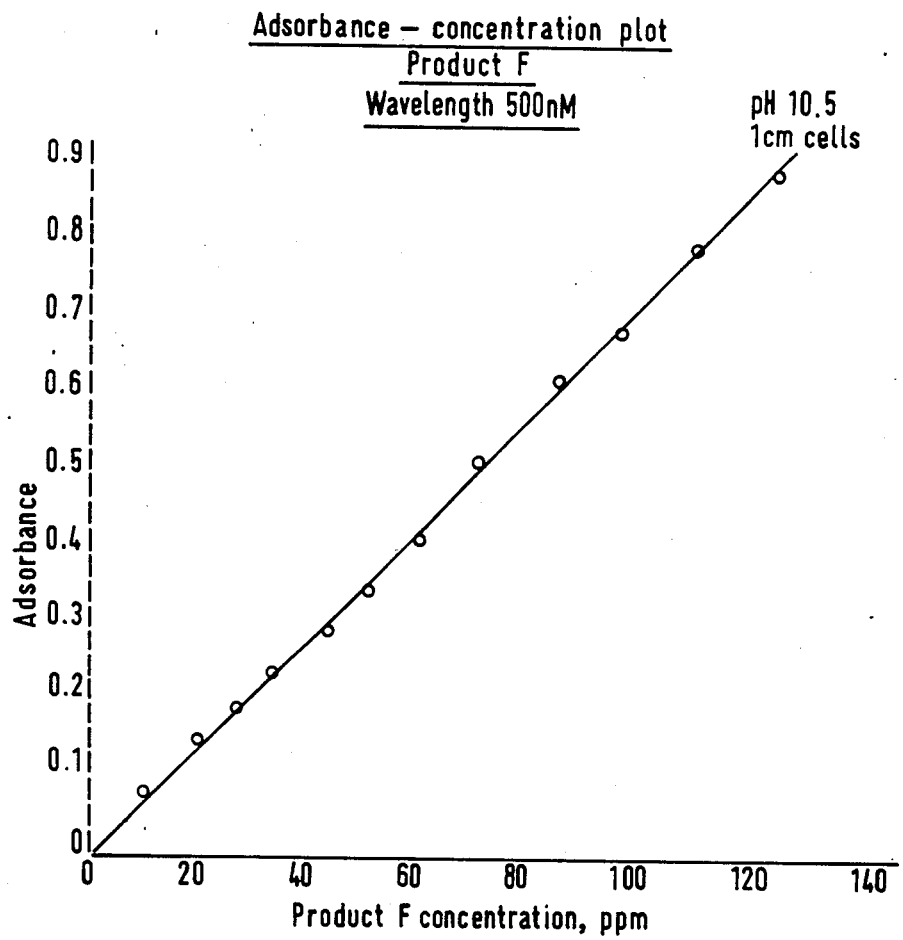

| United States Patent [19] | [11] Patent Number: 4,704,440 |
|---|---|
| Goulding et al. | [45] Date of Patent: Nov. 3, 1987 |

[54] POLYMER COMPOSITIONS DETECTABLE IN WATER

[75] Inventors: John Goulding, Driffield; Derek Clark, Beverley, both of England

[73] Assignee: Bevaloid Limited, Great Britain

[21] Appl. No.: 868,198

[22] Filed: May 23, 1986

Related U.S. Application Data

[63] Continuation of Ser. No. 692,304, Jan. 17, 1985, abandoned.

[30] Foreign Application Priority Data

Jan. 17, 1984 [GB] United Kingdom ................ 8401166

[51] Int. Cl.$^4$ .............................................. C08F 8/00
[52] U.S. Cl. ..................................... 525/376; 526/313;
524/555; 210/96.1; 210/698; 210/701; 210/745; 210/917
[58] Field of Search ........................ 525/376; 526/313; 524/555; 210/917

[56] References Cited

U.S. PATENT DOCUMENTS

| 2,732,382 | 1/1956 | Minsk | 525/376 |
|---|---|---|---|
| 3,380,987 | 4/1968 | Palm | 525/376 |
| 3,597,468 | 8/1971 | Kalopissis | 525/376 |
| 4,065,524 | 12/1977 | Laridon | 525/376 |
| 4,139,697 | 2/1979 | Sidi | 525/376 |
| 4,166,804 | 9/1979 | Bleha | 525/376 |
| 4,487,855 | 12/1984 | Shih | 525/376 |
| 4,525,562 | 6/1985 | Patel | 526/271 |

*Primary Examiner*—Paul R. Michl
*Attorney, Agent, or Firm*—Ostrolenk, Faber, Gerb & Soffen

[57] ABSTRACT

Water treatment, e.g. antiscaling, polymer compositions are marked or labelled with activated groups which are attached to the polymer chain backbone by carbon-carbon bonds. These activated groups are subjected to color forming reactions, e.g. by reaction with a diazonium aromatic compound, thus enabling the polymers to be detected at very low concentrations in water.

20 Claims, 3 Drawing Figures

POLYMER COMPOSITIONS DETECTABLE IN WATER

This is a continuation of application Ser. No. 692,304 filed June 17, 1985 and now abandoned.

This invention relates to polymer compositions detectable in water.

The invention more particularly relates to polymer compositions which are marked or "labelled" with appendant groups which may react with a second component to impart colour to the composition. Such polymer compositions are useful in applications such as antiscaling and water treatment compositions. The polymer compositions according to the invention will normally be soluble or dispersible in water. Whereas the invention will be subsequently described in relation to an anti-scalant composition, it is to be understood that compositions, within the scope of the invention, may be useful in other end-use applications, e.g. as flocculants, textile-treatment polymers or in any polymer composition where it is desirable to monitor low concentrations of polymer.

Scale precipitated from hard water when it is heated causes problems in various industrial operations. It impairs heat-transfer in boilers and condensers, and may block pipe-work. In secondary oil recovery, where water is injected into an oil well in order to displace the crude oil, scale formation may cause blockage of the pores in the oil-bearing strata, thus reducing or even preventing the flow of oil.

A number of companies manufacture low molecular weight polymers which are effective at preventing the deposition of scale from hard water. The necessary treatment is generally at a very low level; a few parts per million (ppm) can have a dramatic antiscaling effect. Although this means that the products are economical in use, checking that they are present at the correct concentration is very difficult. For water systems which are not totally closed, i.e. which have inflow and outflow, the problem is compounded, and arbitrary guesses must be made as to the required rate of antiscalant addition.

The present invention aims to provide a polymer composition which may be detected at very low concentrations in water, for use for example in water treatment such as antiscaling.

The present invention provides a water-soluble or water-dispersible polymer composition, wherein a polymer chain, based on carbon-carbon linkages, has incorporated therein, by means of a functional co-monomer, one or more activated groups which are bonded to the said chain by carbon-carbon linkages, the said activated groups being adapted to react with a group, molecule or radical which imparts colour to the composition, thus allowing the polymer to be detected at very low concentrations.

Preferably the functional co-monomer is an allylic compound.

The polymer chain, in addition to the functional co-monomer, may be suitably composed of one or more co-monomers containing acrylic acid, methacrylic acid, maleic acid, fumaric acid, itaconic acid, citraconic acid, crotonic acid, hydroxy- and sulphonate-functional monomers, hydrocarbon monomers, vinyl esters, vinyl ethers, acrylate esters, methacrylate esters, amides and nitriles.

Preferably the activated group has an aromatic nucleus bearing one or more activating substituents, such as alkoxy, hydroxy or amino groups. Alternatively, the polymer chain may incorporate other active groups known to couple with diazonium compounds to give coloured products. Examples include activated methylene groups such as

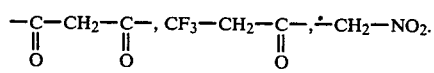

and other compounds which contain highly activated methylene groups.

Preferably the activated group is coupled, during the detection process, with a diazonium compound so as to give a coloured azo-group containing product.

More particularly, the diazonium compound used in the detection process may have an aromatic nucleus with a nitro or other electron—withdrawing group attached to a ring carbon atom.

Alternatively, a diazonium percursor may be present, which under conditions of detection, liberates a diazonium compound, e.g. an aromatic amine, which may be reacted with the activated polymer group in the presence of nitrous acid.

Preferably there is at least one activated group for every 5–50 repeating units of the polymer chain. The precise composition will depend upon, among other things, the concentration at which the polymer needs to be detected, and its molecular weight.

The invention in another aspect provides a method of detecting the presence of a water-treatment polymer in water, by reacting a polymer composition according to the invention with a colour imparting group, molecule or radical.

In the method of the invention, an activated group in the polymer composition may suitably be coupled, during the detection process, with a diazonium compound, to give a coloured azo-group containing product.

The diazonium compound used in the detection process may have an aromatic nucleus with one or more electron-withdrawing groups attached to ring carbon atoms. Alternatively, a diazonium precursor may be present during the detection process, which precursor liberates a diazonium compound.

The invention will be further described with reference to the following illustrative Examples and test data on antiscalant acrylic acid—based polymers, having suitable activated labelling groups, which may be coupled in a detection process with a diazonium compound to give an intensely coloured product.

Polymerization is achieved by normal free radical methods well known in the art, though rather vigorous conditions are required for the allylic and phenolic monomers used. Various initiators and molecular weight regulators may be present.

Example 1 is not according to the invention, in that the polymer produced does not incorporate activated groups linked by carbon-carbon bonds to the polymer backbone. The remaining Examples (2–6) are according to this invention.

EXAMPLE 1

Preparation of an acrylic acid—acetoacetoxyethyl methacrylate copolymer

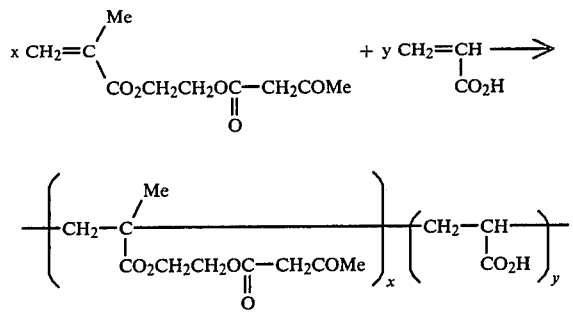

This example is included as an illustration of the problems encountered when the activated labelling group is attached to the polymer chain through an insufficiently hydrolytically—stable grouping, in this case a methacrylate ester.

A mixture of acrylic acid (360 g) and acetoacetoxyethyl methacrylate (40 g) and a solution of ammonium persulphate (20 g) in water (100 g) were added dropwise during 3 hours to boiling water (300 g) which was mechanically agitated. The reaction temperature was kept at 98°-104° C. throughout the additions, and for 30 minutes after. The resulting polymer solution was cooled and neutralised with sodium hydroxide (approx 400 g of 50% aqueous).

The product (referred to as product A) had a viscosity of 1,100 cP (Brookfield LVT viscometer, spindle 2, speed 12 rpm) at 45% non-volatiles and 20° C.

EXAMPLE 2

Preparation of an acrylic acid-o-allylphenol copolymer

The basic reaction for the formation of such a polymer chain is as follows:

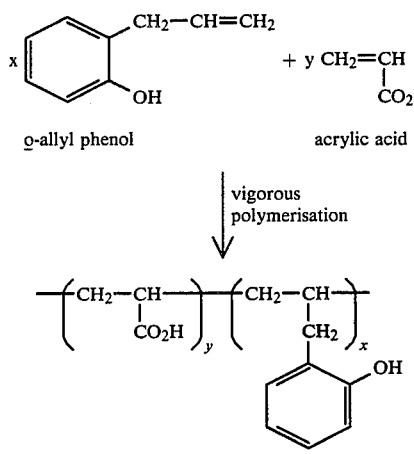

A mixture of acrylic acid (360 g) and o-allylphenol (40 g), a solution of ammonium persulphate (20 g) in water (100 g) and sodium bisulphate (10 g) in water (50 g) were added concurrently during 3 hours to boiling water (250 g) which was mechanically agitated. The reaction temperature was kept at 98°-104° C. throughout the additions and for 30 minutes after. Steam distillation recovered unreacted o-allylphenol (ca. 15% recovery). The resulting polymer solution was cooled and neutralised with sodium hydroxide (approx. 400 g of 50% aqueous).

The product (referred to as product B) had a viscosity of 1,600 cP (Brookfield LVT viscometer, spindle 2, speed 12 rpm) at 45% non-volatiles and 20° C.

Note that in this instance, very vigorous polymerisation conditions of a reducing nature are required for the successful copolymerisation of o-allylphenol.

EXAMPLE 3

Reaction conditions were as in Example 2, except that an addition of mercaptoacetic acid (40 g) was also made concurrently with the other components.

The product (referred to as product C) had a viscosity of 450 cP (Brookfield LVT viscometer, spindle 2, speed 30 rpm) at 45% non-volatiles and 20° C.

EXAMPLE 4

Reaction conditions were as in Example 3, except that 10% of the o-allylphenol was charged into the reaction mixture before the slow additions commenced.

The product (referred to as product D) had a viscosity of 510 cP (Brookfield LVT viscometer, spindle 2, speed 30 rpm) at 45% non-volatiles and 20° C.

EXAMPLE 5

Reaction conditions were as in Example 3, except that part of the acrylic acid (60 g) was added after the main addition of the acrylic acid/o-allylphenol mixture.

The product (referred to as product E) had a viscosity of 480 cP (Brookfield LVT viscometer, spindle 2, speed 30 rpm) at 45% non-volatiles and 20° C.

EXAMPLE 6

Reaction conditions were as in Example 5, except that 3% of the o-allylphenol was charged into the reaction mixture before the other slow additions were commenced.

The product (referred to as product F) had a viscosity of 460 cP (Brookfield LVT viscometer, spindle 2, speed 30 rpm) at 45% non-volatiles and 20° C.

Test for Hydrolytic stability

In use, the labelled scale inhibitor may have to withstand very severe conditions of temperature and pH. The test was designed to assess the resistance of the above-described products to hydrolysis.

50 ppm solutions of each of the above products in distilled water were adjusted to pH 11 with sodium hydroxide, then boiled vigorously under reflux for 48 hours. After this time, the colour intensity given when an excess of p-nitrobenzene diazonium hexafluorophosphate was added was noted in comparison with that given by a fresh, unboiled solution. Product A showed only 35% of the starting colour intensity after boiling, demonstrating extensive loss of the label by hydrolysis. Products B, C, D, E and F were unaffected by boiling, giving colour intensities equal to those of the fresh solution. It is noted that if a few ppm of o-allylphenol are added to the distilled water, a colour is given when p-nitrobenzene diazonium hexafluorophosphate is also present. However, the coloured material in this case is insoluble in water and tends to precipitate out. Also it can be extracted into organic solvents. Colours given by products B, C, D, E and F were totally water-soluble and not extracted into organic solvents.

Proof of attachment of the label

A dilute aqueous solution of Product B was treated with acetone to precipitate the polymer. The precipitate was collected, redissolved in water, and reprecipitated with acetone. This procedure was repeated four times. Finally, the precipitated polymer was dried at 105° C. for 6 hours, and then a 50 ppm solution prepared. Allowing for removal of inorganic salt residues, the colour intensity of this solution when treated with an excess of p-nitrobenzene diazonium hexafluorophosphate under alkaline conditions was comparable with that given by an unpurified solution of Product B.

Performance as scale-inhibitors (i) Calcium carbonate scaling system, static jar-test The procedure adopted was identical to that given in the NACE (National Association of Corrosion Engineers) method TM-03-74, but a brief outline of the test is given below. Varying ppm quantities of scale inhibitors under test were introduced into clean 100 cm$^3$ vessels, followed by 100 cm$^3$ in total of $CO_2$ saturated solutions of synthetic brines (containing $Ca^{2+}$ and $HCO_3^-$ ions). The glass test vessels were firmly stoppered and placed in fan circulated oven operating at 71°±1° C. for a period of time. When this time had elapsed 1 cm$^3$ samples of the hot brine were removed from the test cells, transferred to Erlenmeyer flasks containing distilled water, caustic soda and indicator, and titrated with standard EDTA which thus allowed the evaluation of the unprecipitated $CaCO_3$.

The results thus obtained from this static scaling test method are tabulated in Table 1 below. In the majority of cases, the labelled polymers under investigation yielded results comparable to a standard unlabelled polyacrylate. Similar results for ($Ca^{2+}$) retained in solution were obtained in all cases.

(ii) Calcium carbonate scaling system, dynamic tests.

It is often considered that data gained under dynamic conditions gives a much better insight into the performance of scale inhibitors than that obtained in simple static experiments. In dynamic experiments, where synthetic brines containing 200 ppm $Ca^{2+}$ as the bicarbonate and various additions of antiscalant were passed over a heated, prescaled metal surface at 75° C., larger differences were seen. Products C and F performed, on a polymer for polymer basis, 95% as well as the standard polyacrylate at preventing deposition of scale. Product B only performed 60% as well as the standard.

(iii) $BaSO_4$ and $SrSO_4$—containing systems

Synthetic brines containing 2000 ppm $Ba^{2+}$, 800 ppm $Ca^{2+}$, 100 ppm $Mg^{2+}$, 400 ppm $Sr^{2+}$, 2000 ppm $HCO_3^-$ and 300 ppm $SO_4^{2-}$ were prepared in the presence of varying concentrations of scale inhibiting polymers. The solutions were stored at 82° C. for 48 hours and then examined visually. The results are shown in Table 2 below.

TABLE 2

| POLYMER | POLYMER CONC. | APPEARANCE OF SOLUTION |
|---|---|---|
| Standard polyacrylate scale inhibitor | 10 ppm | Cloudy but well dispersed |
| | 20 ppm | Cloudy, some adherent scale |
| | 30 ppm | Cloudy, some adherent scale |
| | 50 ppm | Cloudy, little adherent scale |
| Product F | 10 ppm | Cloudy but well dispersed |
| | 20 ppm | Cloudy, little adherent scale |
| | 30 ppm | Cloudy, little adherent scale |
| | 50 ppm | V. slight cloudy, no adherent scale. |

Product F was thus seen to perform well in comparison to the standard material in this particularly severe test.

TABLE 1

| POLYMER | POLYMER CONC. (PPM) | CALCIUM CARBONATE RETAINED IN SOLUTION (PPM) TIME IN OVEN | | | | |
|---|---|---|---|---|---|---|
| | | 3 days | 3 days | Average (3 days) | 6 days | 16 hours |
| STANDARD POLYACRYLATE PRODUCT WHICH IS WIDELY USED AS AN ANTI-SCALANT | Blank | 2,480 | 2,500 | 2,490 | 2,530 | 2,650 |
| | 1 | 2,820 | 2,820 | 2,820 | 3,060 | 3,360 |
| | 2 | 3,700 | 3,620 | 3,660 | 3,760 | 3,750 |
| | 5 | 4,100 | 4,100 | 4,100 | 3,960 | 4,040 |
| | 9 | 4,130 | 4,080 | 4,110 | 4,020 | 4,050 |
| | 16 | 4,120 | 4,100 | 4,110 | 4,060 | 4,060 |
| | 25 | 4,080 | 4,120 | 4,100 | 4,070 | 4,070 |
| PRODUCT B | Blank | 2,480 | 2,500 | 2,490 | 2,520 | 2,660 |
| | 1 | 2,630 | 2,710 | 2,670 | 2,940 | 2,940 |
| | 2 | 3,360 | 3,300 | 3,330 | 3,330 | 3,460 |
| | 5 | 3,930 | 3,870 | 3,900 | 3,840 | 3,900 |
| | 9 | 4,100 | 4,040 | 4,070 | 4,000 | 4,070 |
| | 16 | 4,110 | 4,080 | 4,100 | 4,080 | 4,050 |
| | 25 | 4,110 | 4,100 | 4,110 | 4,060 | 4,090 |
| PRODUCT C | Blank | 2,520 | 2,530 | 2,530 | 2,480 | 2,640 |
| | 1 | 2,720 | 2,670 | 2,700 | 2,680 | 3,170 |
| | 2 | 3,600 | 3,570 | 3,590 | 3,580 | 3,830 |
| | 5 | 4,050 | 4,050 | 4,050 | 3,980 | 4,040 |
| | 9 | 3,960 | 4,080 | 4,020 | 4,030 | 4,110 |
| | 16 | 4,020 | 4,100 | 4,060 | 4,100 | 4,080 |
| | 25 | 4,080 | 4,100 | 4,090 | 4,070 | 4,110 |
| PRODUCT F | Blank | 2,520 | 2,510 | 2,520 | 2,520 | 2,650 |
| | 1 | 2,800 | 2,700 | 2,750 | 2,730 | 3,200 |
| | 2 | 3,540 | 3,360 | 3,450 | 3,510 | 3,720 |
| | 5 | 4,040 | 4,030 | 4,040 | 3,960 | 4,060 |
| | 9 | 4,130 | 4,080 | 4,110 | 4,030 | 4,060 |
| | 16 | 4,110 | 4,120 | 4,120 | 4,080 | 4,050 |
| | 25 | 4,130 | 4,120 | 4,130 | 4,060 | 4,060 |

Detection procedure

The following samples to serve to illustrate the ease and reproducibility with which detection of the polymer can be achieved.

The pendant activated aromatic nuclei contained in the Products B, C, D, E and F will couple with diazonium compounds (e.g. p-nitrobenzene diazonium hexafluorophosphate) to give an intense colour which is easily visually detectable at the level of parts per million in aqueous solution. This is depicted in the reaction scheme below:

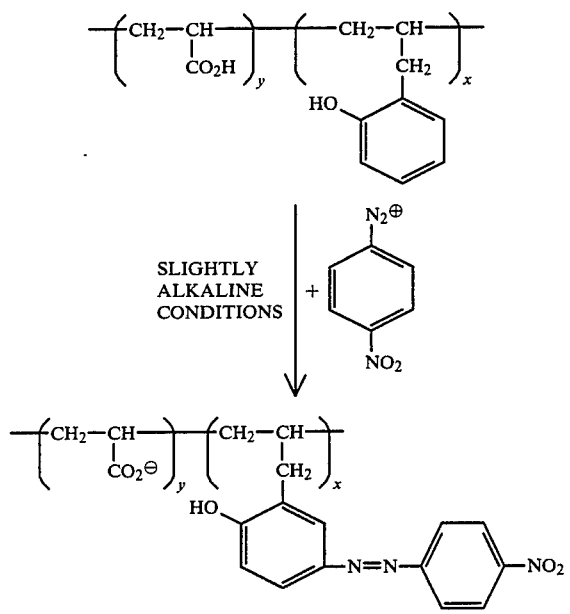

The concentration of the phenolically-labelled antiscalant polymer in treated water can be readily monitored visually or spectroscopically, simply by adding an excess of a diazonium compound to a sample of the water which has been made mildy alkaline. It may be possible to automate the system so that dosage of antiscalant is controlled by a signal from a spectrophotometer.

Naturally any diazonium compound capable of giving a useful colour may be used in the detection step. Especially favoured are those, such as nitro-functional compound, zinc complexes or zwitterions, which are relatively stable and may be stored for reasonable periods of time.

Conveniently the diazonium compound and any other chemicals may be added to the water sample in the form of tablet(s).

The colour strength and hue of the azo compound formed in the detection process is to a degree dependent upon pH, and so systems under test need to be buffered to a similar value. Colour strength is directly proportional to concentration of the labelled polymer, as shown in FIG. 1 of the accompanying drawings which is a graph of adsorbance versus concentration in respect of the product F of Example 6 (at wavelength 500 nM).

Figure 2:
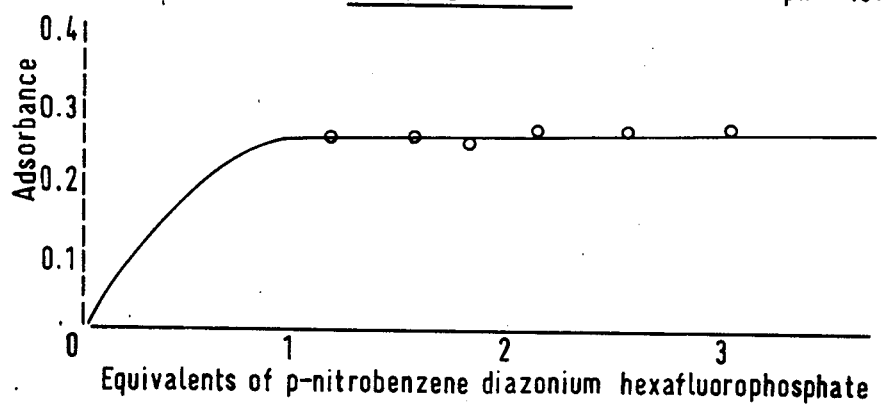
Figure 3:
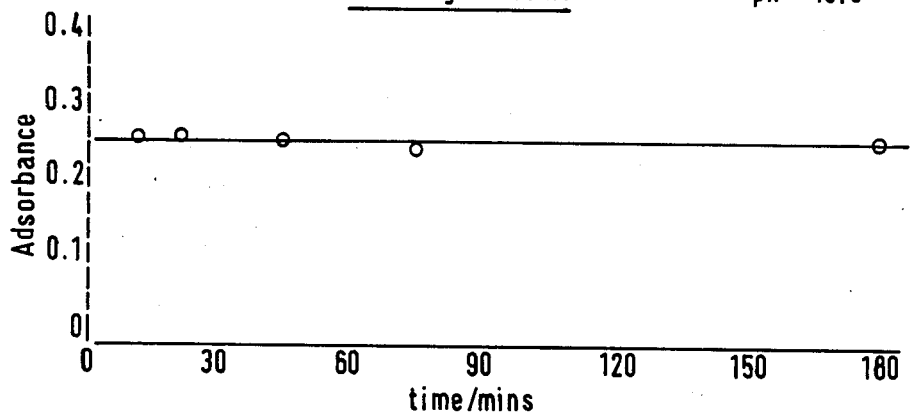

Excess of detection reagent within reasonable limits does not cause change in colour intensity or hue over the usual experimental timescale. Once developed, the colours are quite stable for several hours at least, as indicated by FIGS. 2 and 3 of the accompanying drawings. FIG. 2 indicates the influence of excess detection reagent on recorded absorbance by means of a graph of adsorbance versus equivalents of p-nitrobenzene diazonium hexafluorophosphate in respect of the product F of Example 6 (at wavelength 500 nM), while FIG. 3 indicates the effect of time on recorded absorbance by means of a graph of absorbance versus time/mins in respect of the product F (at wavelength 500 nM).

In practice, the detection procedure outlined above lends itself readily either for comparison of the colour intensity of the unknown solution with that given by a standard, or with the disc of a colour comparator. Such techniques are well known and generally used with a variety of other colourimetric systems.

Adsorption Studies

Clearly it is an important aspect of this invention that a label is firmly attached to the polymer chain, by carbon-carbon bonds, and essentially inseparable from it. This is important because in many uses, particularly during secondary oil recovery, the treated water may come into contact with large areas of potentially absorbent surfaces. It is vital that there is no possiblity that substantial fractionation of the labelled material will occur. Naturally, the likelihood of adsorptive separation precludes the simple "spiking" of a conventional antiscalant polymer solution with a readily—detectable marker. However, certain precautions also need to be taken when the labelled polymer systems of this invention are synthesised. Care is required to ensure that the molecular weight distribution of the polymer and the distribution of the labelling co-monomer are such that the product is sufficiently homogeneous to preclude adsorptive fractionation. Methods of such protection control are known by those familiar with the art.

In order to test the polymers described in the examples, adsorption studies were done on a variety of surfaces: $CaCO_3$, $Fe_2O_3$, $TiO_4$, $BaSO_4$, $SiO_2$ and activated charcoal. Adsorption of polymer was followed by both the colourimetric procedure, and also by potentiometric titration. This allowed a comparison between the known concentration of polymer in solution from the titration, with that given by the colourimetric method. Deviations between the two values are caused by selective adsorption of a polymer fraction. With most substrates, little problem was found with any of the Products B, C, D, E or F. However, activated charcoal presented a particularly severe test. This is probably due to the carbon surface offering a particularly suitable site for adsorption of the phenolic labelling functions, and also its microporosity aiding fractionation by molecular size.

Experimental details 50 ml samples of 2,500 ppm solutions of each of the polymers were contacted with activated charcoal at pH 3 for 48 hours. The charcoal was then filtered off and the filtrate tested both by potentiometric titration and (after suitable dilution) colourimetrically with p-nitrobenzene diazonium hexafluorophosphate. The results are shown in Table 3 below.

TABLE 3

| POLYMER SYSTEM | Ratio of $\dfrac{\text{colourimetric determination of adsorbed polymer}}{\text{titration value of adsorbed polymer}}$ |
|---|---|
| PRODUCT C | 1.90 |
| PRODUCT D | 1.59 |
| PRODUCT E | 1.35 |

TABLE 3-continued

| POLYMER SYSTEM | Ratio of colourimetric determination of adsorbed polymer / titration value of adsorbed polymer |
|---|---|
| PRODUCT F | 1.05 |

As can be seen, when the polymer is synthesised under conditions conducive to obtaining a homogenous product, good arrangement is obtained between the two techniques and no problems with selective adsorption will occur. High values are indicative of a poorer distribution of the labelling co-monomer throughout the polymer composition.

Interference with detection by contaminating species

In order to be a useful indicator of polymer concentration, the intensity and hue of the colour given by the labelled polymers must be reasonably independent of other species present in solution. This has been found to be largely so. Colour is unaffected by electrolyte concentration and most other species often present in water-treatment compositions, e.g. phosphonates, polyphosphates, aliphatic amines. Cationic species of the type often used as biocides may cause a shift in colour hue towards the violet end of the spectrum. If such materials are present in the water sample, it is desirable to add an excess of a cationic surfactant during the detection process to eliminate any errors due to variation in the concentration of the biocide. This change in hue with cationic species in a useful additional diagnostic tool, especially is contaiminating species make detection at the red end of the spectrum difficult. Some crude oils contain traces of phenolic materials which may give transient colours with the diazonium detection reagent. However, these colours tend to fade as the azo compounds formed are not water-soluble and precipitate out. Such colours are also readily extracted into organic solvents; simply shaking the water sample with a small amount of a suitable solvent was found to eliminate the interfering effect. Water-soluble phenolic compounds (eg lignosulphonates) will also give colours with diazonium compounds. These are generally of a different hue to those given by the labelled polymers of the invention, and it is possible to check the composition of mixtures of lignosulphonates and labelled polymers by examination of the hue visually or spectroscopically. Very strongly oxidising or reducing water systems could cause bleaching of the azo compound in the detection process, and for such systems it is useful to bring the system to a reasonably neutral redox potential before analysis.

We claim:

1. A two part composition for water treatment and detection of the water treatment chemical comprising a first reagent which is a water treatment chemical, said water treatment chemical being a water-soluble polymer which has a carbon-carbon polymer chain and has incorporated therein by means of a functional comonomer at least one activated group for every 5–50 repeating units of the polymer chain, the activated group being bonded to said chain by linkages consisting of carbon-carbon linkages and said activated group being adapted to react with a moiety which interacts to impart color to the polymer and being selected from the group consisting of an aromatic nucleus bearing at least one activating substituent and an activated methylene group, thus allowing the polymer to be detected at very low concentrations, and a second reagent which is a moiety which interacts with said water treatment polymer to produce color.

2. A composition according to claim 1 in which the second reagent is a diazonium compound, adapted to give a colored azo-group containing product upon said interaction.

3. In a water treatment method in which a water treatment chemical is introduced into water, the improvement which comprises (1) employing a water-soluble polymer which has a carbon-carbon polymer chain having incorporated therein by means of a functional comonomer at least one activated group for every 5–50 repeating units of the polymer chain, the activated group bonded to said chain by linkages consisting of carbon-carbon linkages and said activated group being adapted to react with a moiety which imparts color to the polymer and being selected from the group consisting of an aromatic nucleus bearing at least one activating substituent and an activated methylene group, thus allowing the polymer to be detected at very low concentrations as the water treatment chemical and (2) detecting the presence or quantity of said water treatment chemical by obtaining a sample of the water, combining the sample with a moiety which interacts with said water treatment chemical to produce color and determining the color of the resulting water sample.

4. The method according to claim 3 in which the functional comonomer is an allylic compound.

5. The method according to claim 3 in which the polymer chain in addition to the functional comonomer, is composed of residues derived from at least one of acrylic acid and methacrylic acid.

6. The method of claim claim 5 in which the water treatment chemical is a copolymer of o-allylphenol and acrylic acid.

7. The method of claim 3 in which an additional quantity of said water treatment chemical is introduced into the water and the amount of the additional quantity is determined based on the result of said determination step.

8. The method of claim 3 in which said moiety is introduced into the water sample in the form of a tablet.

9. A composition according to claim 1 in which said water treatment polymer is a copolymer of o-allylphenol and acrylic acid.

10. A composition according to claim 1 in which said moiety is in the form of a tablet.

11. The composition according to claim 1, wherein the functional co-monomer is an allylic compound.

12. The composition according to claim 1, wherein the polymer chain, in addition to the functional co-monomer, is composed of residues derived from at least one of acrylic acid and methacrylic acid.

13. The composition according to claim 1, wherein the activated group in the functional co-monomer is an aromatic nucleus bearing at least one activating substituent.

14. The composition according to claim 13, wherein the activating substituent is selected from the group consisting of alkoxy, hydroxy and amino groups.

15. The composition according to claim 1, wherein the activated group in the functional co-monomer is an activated methylene group.

16. The composition according to claim 2, wherein the diazonium compound has an aromatic nucleus with at least one electron—withdrawing group attached to ring carbon atoms.

17. The composition according to claim 16, wherein the electron—withdrawing group is a nitro group.

18. The method according to claim 3, wherein an activated group in the polymer composition is coupled, during the detection process, with a diazonium compound, to give a coloured azo-group containing product.

19. The method according to claim 18, wherein the diazonium compound used in the detection process has an aromatic nucleus with at least one electron-withdrawing group attached to ring carbon atoms.

20. the method according to claim 18, wherein a diazonium precursor is present during the detection process, which precursor liberates a diazonium compound.

* * * * *